(12) United States Patent
Fu

(10) Patent No.: US 11,829,390 B2
(45) Date of Patent: Nov. 28, 2023

(54) RECIPE CONSTRUCTION SYSTEM, RECIPE CONSTRUCTION METHOD, COMPUTER READABLE RECORDING MEDIA WITH STORED PROGRAMS, AND NON-TRANSITORY COMPUTER PROGRAM PRODUCT

(71) Applicant: WALSIN LIHWA CORPORATION, Taipei (TW)

(72) Inventor: Yu-Hsiang Fu, Taipei (TW)

(73) Assignee: WALSIN LIHWA CORPORATION, Taipei (TW)

( * ) Notice: Subject to any disclaimer, the term of this patent is extended or adjusted under 35 U.S.C. 154(b) by 7 days.

(21) Appl. No.: 17/562,066

(22) Filed: Dec. 27, 2021

(65) Prior Publication Data
US 2023/0081281 A1   Mar. 16, 2023

(30) Foreign Application Priority Data
Sep. 14, 2021   (TW) .................................. 110134295

(51) Int. Cl.
*G06F 16/28*   (2019.01)
*G06N 3/08*    (2023.01)

(52) U.S. Cl.
CPC ............. *G06F 16/285* (2019.01); *G06N 3/08* (2013.01)

(58) Field of Classification Search
CPC .......... G06F 16/285; G06N 3/08; G06N 3/02; G06N 3/047; G06T 2207/30164;
(Continued)

(56) References Cited

U.S. PATENT DOCUMENTS

2010/0332475 A1\* 12/2010 Birdwell ............. G06F 18/2323
                                                707/E17.014
2013/0223724 A1   8/2013 Wersborg et al.
(Continued)

FOREIGN PATENT DOCUMENTS

| CN | 111753752 A | 10/2020 |
| TW | 202044095 A | 12/2020 |

(Continued)

*Primary Examiner* — Evan Aspinwall
(74) *Attorney, Agent, or Firm* — McClure, Qualey & Rodack, LLP

(57) ABSTRACT

A recipe construction system, a recipe construction method, a computer readable recording media with stored programs, and a non-transitory computer program product are provided. A dimension reduction module obtains dimension-reduced composition information according to composition information of each piece of historical recipe information and a dimension reduction algorithm. A neural network module obtains a plurality of trained neural network parameters according to the composition information and the dimension reduction composition information. The neural network module obtains dimension-reduced initial composition information according to the trained neural network parameters and initial composition information. A search module searches the historical recipe information for a first quantity of pieces of candidate recipe information. A determining module determines whether physical property information of each piece of candidate recipe information meets a specification, and outputs solution recipe information that meets the specification.

16 Claims, 10 Drawing Sheets

(58) Field of Classification Search
CPC . G06T 2207/30156; G06T 2207/20081; G06T 7/0004; B23K 2101/34; B23K 2103/08; B23K 2103/02; B23K 26/32; B23K 26/322; B23K 28/02; G05B 19/41875; G05B 19/4083; G05B 13/0285; G16C 20/70; G16C 20/10; G16C 20/30; G16C 60/00; B33Y 10/00; B33Y 80/00
USPC .................... 707/769; 715/753; 700/119, 47; 705/7.23
See application file for complete search history.

(56) References Cited

U.S. PATENT DOCUMENTS

| | | | |
|---|---|---|---|
| 2018/0243800 A1 | 8/2018 | Kumar et al. | |
| 2020/0293945 A1* | 9/2020 | Liu | G06N 3/044 |
| 2021/0349299 A1 | 11/2021 | Wang et al. | |
| 2022/0383344 A1* | 12/2022 | Soderberg | G06Q 30/0205 |

FOREIGN PATENT DOCUMENTS

| | | |
|---|---|---|
| TW | 732544 B | 7/2021 |
| TW | I732544 B | 7/2021 |

\* cited by examiner

RECIPE CONSTRUCTION SYSTEM, RECIPE CONSTRUCTION METHOD, COMPUTER READABLE RECORDING MEDIA WITH STORED PROGRAMS, AND NON-TRANSITORY COMPUTER PROGRAM PRODUCT

CROSS-REFERENCE TO RELATED APPLICATION

This non-provisional application claims priority under 35 U.S.C. § 119(a) to Patent Application No. 110134295 in Taiwan, R.O.C. on Sep. 14, 2021, the entire contents of which are hereby incorporated by reference.

BACKGROUND

Technical Field

The present invention relates to the field of recipe construction, and in particular, to a technology of applying a neural network to integrating experiential knowledge to construct recipes.

Related Art

A dose-response relationship is a form of a change relationship between input and output variables, and has the same form in different processes, for example, a relationship between a chemical raw material combination of a wire-and-cable recipe design (an input) and a physical property of a finished coating material (an output), a relationship between controllable machine parameters of a wire-and-cable flexible copper wire drawing process (an input) and physical properties of a wire-rod (an output), a relationship between machine controllable parameters of a cold/hot steel rolling process (an input) and quality characteristics of a finished product (an output), or a relationship between controllable parameters of an acid-pickling process of a stainless steel finished product (a plate, a bar, or a wire-rod) (an input) and weight consumption of the finished product (an output). However, conventionally, in an actual application, the construction of the foregoing dose-response relationship usually relies mainly on trials and errors of human experience, and knowledge generated and accumulated from past successful experience cannot be effectively used.

SUMMARY

In view of this, some embodiments of the present invention provide a recipe construction system, a recipe construction method, a computer readable recording media with stored programs, and a non-transitory computer program product, to alleviate existing technical problems.

An embodiment of the present invention provides a recipe construction system. The recipe construction system includes a dimension reduction module, a neural network module, a search module, and a determining module. The dimension reduction module is configured to receive a plurality of pieces of historical recipe information, and obtain a piece of dimension-reduced composition information of each of the plurality of pieces of historical recipe information according to a piece of composition information of each of the plurality of pieces of historical recipe information and a dimension reduction algorithm. The neural network module is configured to receive a piece of initial composition information, where the neural network module is configured to train a plurality of neural network parameters of the neural network module according to the piece of composition information and the piece of dimension-reduced composition information of each of the plurality of pieces of historical recipe information to obtain a plurality of trained neural network parameters. The neural network module is further configured to obtain a piece of dimension-reduced initial composition information according to the trained neural network parameters and the piece of initial composition information. The search module is configured to search the plurality of pieces of historical recipe information for a first quantity of pieces of candidate recipe information according to a first distance metric, the piece of dimension-reduced initial composition information, and the piece of dimension-reduced composition information of each of the plurality of pieces of historical recipe information. In addition, the determining module is configured to determine whether a piece of physical property information of each the first quantity of pieces of candidate recipe information meets a specification, and output a piece of solution recipe information in response to the piece of physical property information of the piece of solution recipe information in the first quantity of pieces of candidate recipe information meets the specification.

An embodiment of the present invention provides a recipe construction method, performed by a processor. The recipe construction method includes the following steps: receiving a plurality of pieces of historical recipe information, and obtaining a piece of dimension-reduced composition information of each of the plurality of pieces of historical recipe information according to a piece of composition information of each of the plurality of pieces of historical recipe information and a dimension reduction algorithm; receiving a piece of initial composition information, training a plurality of neural network parameters of a neural network module according to the piece of composition information and the piece of dimension-reduced composition information of each of the plurality of pieces of historical recipe information to obtain a plurality of trained neural network parameters, and obtaining a piece of dimension-reduced initial composition information according to the trained neural network parameters and the piece of initial composition information; searching the plurality of pieces of historical recipe information for a first quantity of pieces of candidate recipe information according to a first distance metric, the piece of dimension-reduced initial composition information, and the piece of dimension-reduced composition information of each of the plurality of pieces of historical recipe information; and determining whether a piece of physical property information of each the first quantity of pieces of candidate recipe information meets a specification, and outputting a piece of solution recipe information in response to the piece of physical property information of the piece of solution recipe information in the candidate recipe information meets the specification.

The present invention provides a computer readable media with stored programs and a non-transitory computer program product. After loading and executing the stored programs, a processor can complete the foregoing recipe construction method.

Based on the above, some embodiments of the present invention provide the recipe construction system, the recipe construction method, the computer readable recording media with stored programs, and the non-transitory computer program product. The dimension reduction module receives a plurality of pieces of historical recipe information, and obtains a piece of dimension-reduced composition information of each of the plurality of pieces of historical recipe information according to a piece of composition information of each of the plurality of pieces of historical recipe information and a dimension reduction algorithm. The neural network module receives a piece of initial composition information, and trains a plurality of neural network parameters of the neural network module according to the piece of composition information and the piece of dimension-reduced composition information of each of the plurality of pieces of historical recipe information to obtain a plurality of trained neural network parameters. The neural network module further obtains a piece of dimension-reduced initial composition information according to the trained neural network parameters and the piece of initial composition information. The search module is configured to search the plurality of pieces of historical recipe information for a first quantity of pieces of candidate recipe information according to a first distance metric, the piece of dimension-reduced initial composition information, and the piece of dimension-reduced composition information of each of the plurality of pieces of historical recipe information. In addition, the determining module is configured to determine whether a piece of physical property information of each the first quantity of pieces of candidate recipe information meets a specification, and output a piece of solution recipe information in response to physical property information of the piece of solution recipe information in the first quantity of pieces of candidate recipe information meets the specification, to automatically and effectively use knowledge included in the plurality of pieces of historical recipe information.

DETAILED DESCRIPTION

Figure 1A:
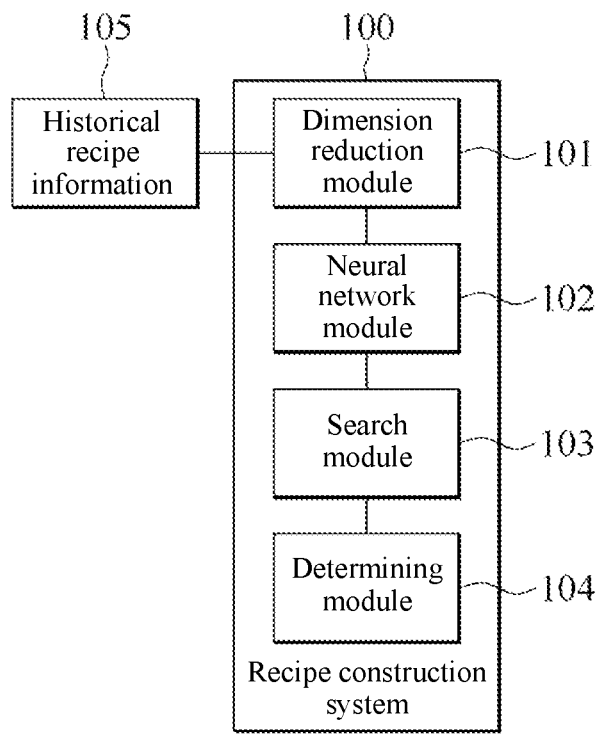
FIG. 1A is a block diagram of a recipe construction system and historical recipe information according to an embodiment of the present invention.

The above and other technical contents, features, and effects of the present invention can be clearly presented below in the following detailed description of the embodiments with reference to the accompanying drawings. The proportions or sizes of elements in the drawings expressed in an exaggerated, omitted, or general manner are used to help a person skilled in the art to understand and read, are not intended to define restraint conditions under which the present invention can be implemented, and therefore, have no technical significance. Any modification to the structure, change to the proportional relationship, or adjustment on the size should fall within the scope of the technical content disclosed by the present invention without affecting the effects and the objectives that can be achieved by the present invention. The same reference numerals are used to indicate the same or similar elements in all of the drawings. The term "couple" or "connect" mentioned in the following embodiments may refer to any direct or indirect, or wired or wireless connection means.

Figure 1B:
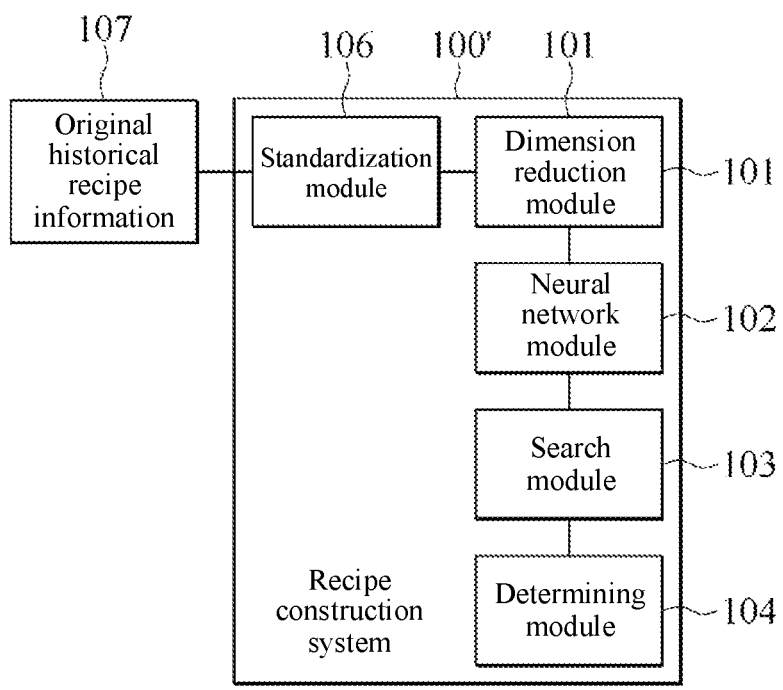
FIG. 1B is a block diagram of a recipe construction system and original historical recipe information according to an embodiment of the present invention.

FIG. 1A is a block diagram of a recipe construction system 100 and a plurality of pieces of historical recipe information 105 according to an embodiment of the present invention. FIG. 1B is a block diagram of a recipe construction system 100 and a plurality of pieces of original historical recipe information 107 according to an embodiment of the present invention. Refer to FIG. 1A and FIG. 1B together. As shown in FIG. 1A, in a software implementation, the recipe construction system 100 includes a dimension reduction module 101, a neural network module 102, a search module 103, and a determining module 104. The dimension reduction module 101 is configured to receive the plurality of pieces of historical recipe information 105.

Each of the plurality of pieces of historical recipe information 105 includes a piece of composition information and a piece of physical property information. In this embodiment, the piece of composition information includes a quantity of each chemical raw material. The piece of physical property information includes a physical property of a finished product. The piece of composition information and the piece of physical property information are presented in a vector form. For example, the piece of composition information is presented in the form of the following composition information vector:

(1.0, 2.0, 1.5, 4, 2.3, 1.7, 10).

Components of the composition information vector represent different chemical raw material ingredients, and values of the components represent doses of the different chemical raw material ingredients during manufacturing. For example, the first component represents a dose of the first type of principal plastic material, the second component represents a dose of the second type of principal plastic rubber, and a third component represents a dose of the first type of filler. Information displayed in the composition information vector is the piece of composition information.

The piece of physical property information is presented in the form of the following physical property information vector:

(1.12, 341, 33.67, 5.52).

Components of the physical property information vector represent different physical properties. The physical properties are physical properties of a finished product manufactured by using corresponding composition information. For example, the first component of the physical property information vector represents tensile strength, the second component represents a percentage of elongation, the third component represents viscosity of a plastic mixture, and the fourth component represents compression deformation. Information displayed in the physical property information vector is the piece of physical property information.

It should be noted that, although in this embodiment, the piece of composition information includes the quantity of each chemical raw material, and the piece of physical property information includes the physical property of the finished product, in an embodiment of the present invention, the piece of composition information includes a controllable parameter of a wire-and-cable flexible copper wire drawing process, and the piece of physical property information includes a physical property of a wire rod; in an embodiment of the present invention, the piece of composition information includes controllable machine parameters of a cold/hot steel rolling process, and the piece of physical property information includes quality characteristics of a finished product; in an embodiment of the present invention, the piece of composition information includes controllable parameters of an acid cleaning process of a stainless steel finished product (a plate, a bar, or a wire-rod), and the piece of physical property information includes weight consumption of the finished product, provided that the piece of composition information and the piece of physical property information include a relationship of interaction. The present invention is not limited thereto. In addition, although in this embodiment, the piece of composition information and the piece of physical property information are presented in a vector form, the piece of composition information and the piece of physical property information may alternatively be presented in a matrix form. The present invention is not limited thereto.

The recipe construction system 100 receives a specification from the outside. The neural network module 102 of the recipe construction system 100 receives a piece of initial composition information from the outside. An objective of the recipe construction system 100 is to output, according to the piece of initial composition information received from the outside and the plurality of pieces of historical recipe information 105, a composition information vector that can be used for manufacturing a finished product of which physical properties meet the specification, that is, output the piece of composition information represented by the composition information vector.

In this embodiment, the specification is a set of physical property limit ranges. Using the foregoing physical property information vector as an example, the specification is: tensile strength >13, percentage of elongation >300, viscosity of plastic mixture >20, and compression deformation <10.

In this embodiment, the composition information vectors of the plurality of pieces of historical recipe information 105 received by the dimension reduction module 101 are values after standardizing. That is, values of components of each of the composition information vector are values obtained by standardizing an original composition information vector representing one of the plurality of pieces of original historical recipe information. In this embodiment, the standardization is to first subtract corresponding means from an original composition information vector of each piece of original historical recipe information, and then divide by a corresponding standard deviation. For example, the plurality of pieces of original historical recipe information are represented by using the following three groups of vectors:

a first group: an original composition information vector (273, 82, 105, 210, 9, 904, 680), and a physical property information vector (23, 62, 34.99);

a second group: an original composition information vector (163, 149, 191, 180, 12, 843, 746), and a physical property information vector (0, 20, 41.14); and a third group: an original composition information vector (162, 148, 191, 179, 16, 840, 743), and a physical property information vector (1, 20, 41.81).

A mean of the first components of the original composition information vectors is (273+163+162)/3=199.33, and a standard deviation is 52.09. Values of the first components of all the original composition information vectors are then normalized by using the mean, 199.3, of the first components of the original composition information vectors, the standard deviation 52.09, and a formula $$\frac{x-\mu}{\sigma},$$

to obtain (273−199.3)/52.09=1.41, (163−199.3)/52.09=−0.69, and (162−199.3)/52.09=−0.71. In this way, the standardization of the first components of the original composition information vectors is completed. The foregoing steps are repeated to standardize each component of each original composition information vector, to obtain a composition information vector of the historical recipe information 105. A mean and a standard deviation of each component of the original composition information vector are referred to as standardization parameters.

It should be noted that, the foregoing standardization method is not the only method. Appropriate standardization parameters may be selected according to a characteristic of actual data to standardize original composition information.

Referring to FIG. 1B, in an embodiment of the present invention, a recipe construction system 100' further includes a standardization module 106. The standardization module 106 is configured to receive the plurality of pieces of original historical recipe information 107, standardize the plurality of pieces of original historical recipe information 107 according to the foregoing method, to obtain the piece of composition information of each of the plurality of pieces of historical recipe information 105, and then transmit the plurality of pieces of historical recipe information 105 to the dimension reduction module 101.

The recipe construction method and the cooperation between the modules of the recipe construction systems 100 and 100' in the embodiments of the present invention are described in detail below with reference to the drawings.

Figure 3:
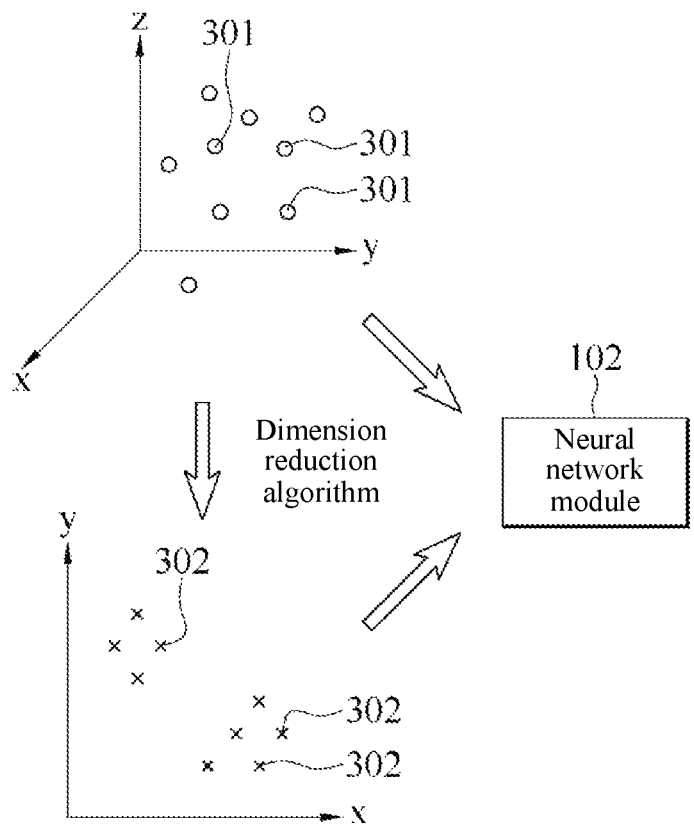
FIG. 3 is a schematic diagram of operation of a dimension reduction module and a neural network module according to an embodiment of the present invention.
Figure 9:
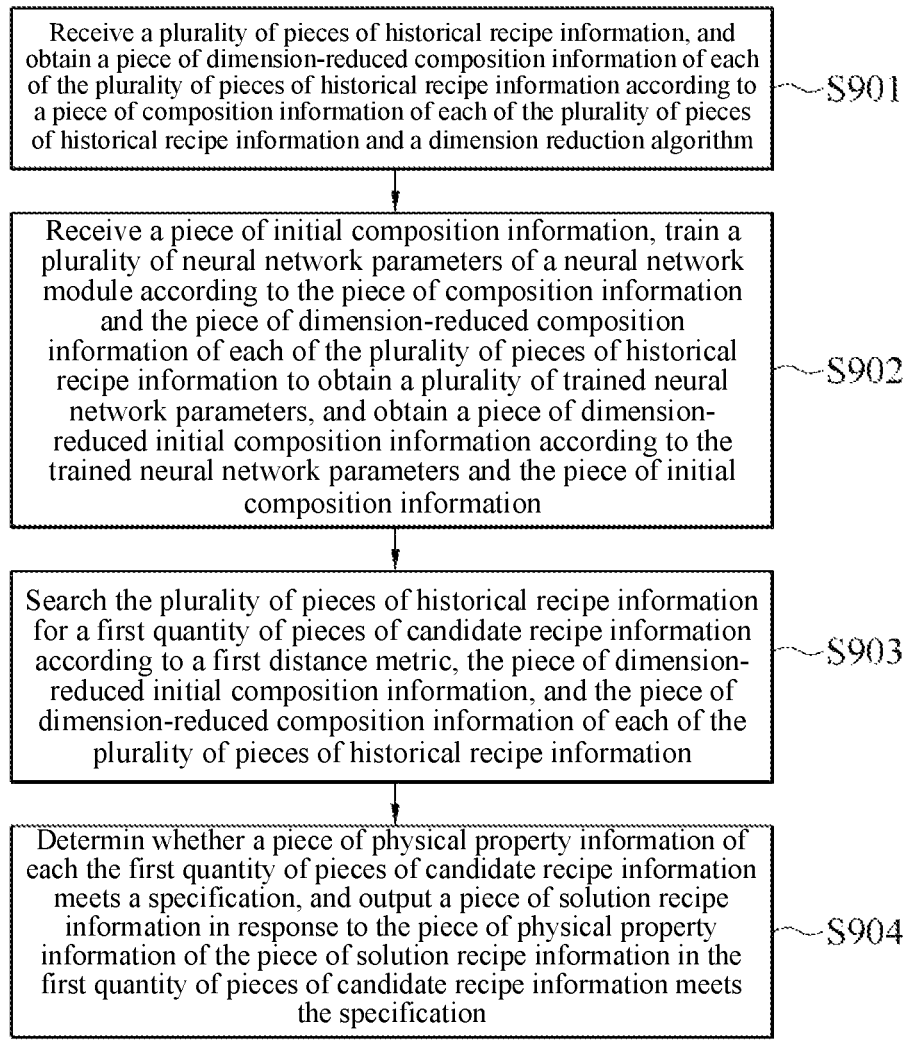
FIG. 9 is a flowchart of a recipe construction method according to an embodiment of the present invention.

FIG. 3 is a schematic diagram of operation of a dimension reduction module 101 and a neural network module 102 according to an embodiment of the present invention. FIG. 9 is a flowchart of a recipe construction method according to an embodiment of the present invention. Refer to FIG. 1A, FIG. 1B, FIG. 3, and FIG. 9 together. In step S901, the dimension reduction module 101 receives a plurality of pieces of historical recipe information 105, and obtain a piece of dimension-reduced composition information of each of the plurality of pieces of historical recipe information 105 according to a piece of composition information of each of the plurality of pieces of historical recipe information 105 and a dimension reduction algorithm.

In this embodiment, as shown in FIG. 3, the dimension reduction module 101 reduces dimension of composition information vectors 301 of all the plurality of pieces of historical recipe information 105 by using a t-distributed stochastic neighbor embedding (t-SNE) algorithm as a dimension reduction algorithm, to obtain dimension-reduced composition information vectors 302. The dimension-reduced composition information vectors 302 are in a two-dimensional vector space.

In step S902, the neural network module 102 trains a plurality of neural network parameters of the neural network module 102 by using the composition information vector 301 of each of the plurality of pieces of historical recipe information 105 and the corresponding dimension-reduced composition information vector 302 as training samples, to obtain a plurality of trained neural network parameters. That is, in this embodiment, an internal process of the dimension reduction algorithm is learned by using the plurality of neural network parameters of the neural network module 102. After obtaining the trained neural network parameters, the neural network module 102 receives a piece of initial composition information from the outside, where in this embodiment, the piece of initial composition information is represented by using an initial composition information vector; and obtains a piece of dimension-reduced initial composition information according to the trained neural network parameters and the piece of initial composition information. The initial composition information vector has been standardized by using the mean and the standard deviation (that is, the standardization parameters) of each component of the foregoing original composition information vector (in the embodiment shown in FIG. 1B, the standardization module 106 first receives the plurality of pieces of original initial composition information, and the standardization module 106 then performs standardization by using the mean and the standard deviation of the each component of the foregoing original composition information vector to obtain initial composition information, and then transmits the piece of initial composition information to the neural network module 102 to obtain the piece of dimension-reduced initial composition information).

In the foregoing process of learning the internal process of the dimension reduction algorithm by using the neural network module 102, the corresponding dimension-reduced composition information vector 302 may be obtained without affecting the dimension reduction process of the composition information vector 301 of the plurality of pieces of historical recipe information 105 by the piece of initial composition information, to maintain the independence of the dimension-reduced composition information vector 302 and prevent the dimension-reduced composition information vector 302 from being affected by the piece of initial composition information.

In some embodiments of the present invention, the dimension reduction module 101 uses another nonlinear algorithm (for example, a locally linear embedding (LLE) algorithm or an isometric mapping algorithm) as the dimension reduction algorithm. The present invention does not limit a type of the nonlinear algorithm.

In some embodiments of the present invention, the dimension reduction module 101 uses a linear algorithm (for example, principal component analysis (PCA)) as the dimension reduction algorithm.

Figure 4:
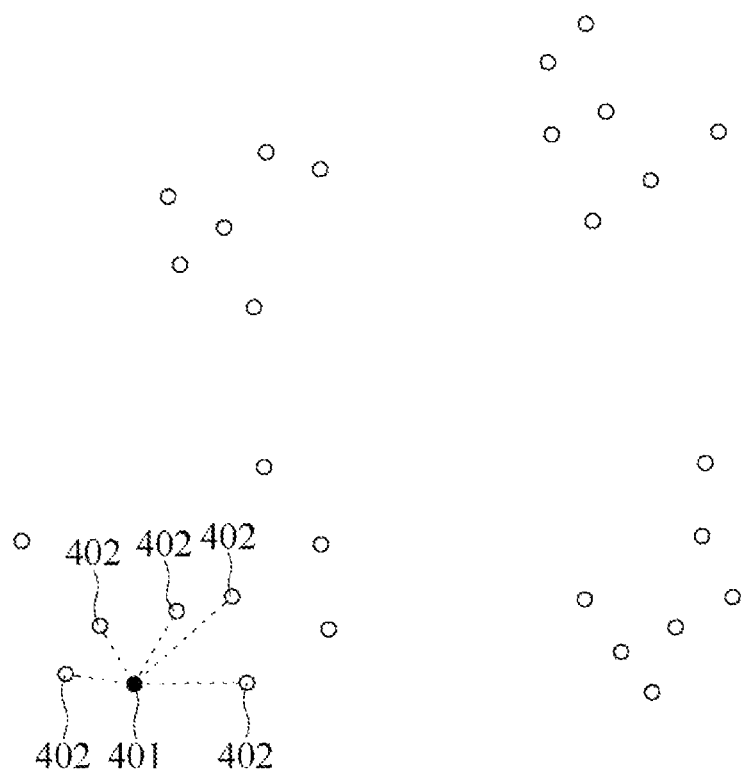
FIG. 4 is a schematic diagram of operation of a search module according to an embodiment of the present invention.

FIG. 4 is a schematic diagram of operation of a search module 103 according to an embodiment of the present invention. Refer to FIG. 4.

In step S903, the search module 103 searches the plurality of pieces of historical recipe information 105 for a first quantity of pieces of candidate recipe information according to a first distance metric, the piece of dimension-reduced initial composition information, and the piece of dimension-reduced composition information of each of the plurality of pieces of historical recipe information 105.

In this embodiment, the search module 103 searches, according to a first distance metric (the Euclidean distance in a two-dimensional vector space in this embodiment), the historical recipe information vectors for a first quantity (the first quantity in the example shown in FIG. 4 is 5) of dimension-reduced composition information vectors 402 closest to the dimension-reduced initial composition information vector 401. The search module 103 then searches for a first quantity of pieces of historical recipe information corresponding to the dimension-reduced composition information vectors 402. The first quantity of pieces of historical recipe information are referred to as the first quantity of pieces of candidate recipe information for the convenience of the following description.

In step S904, after the first quantity of pieces of candidate recipe information are selected, the determining module 104 then determines whether there is any piece of physical property information that meets a specification in physical property information of the first quantity of pieces of candidate recipe information. If there is one or more pieces of physical property information that meets the specification in the physical property information of the first quantity of pieces of candidate recipe information, for the convenience of description, the plurality of pieces of candidate recipe information corresponding to the physical property information that meets the specifications is referred to as a plurality of pieces of solution recipe information. The determining module 104 then outputs the plurality of pieces of solution recipe information.

It should be noted that, although in the foregoing embodiments, the first distance metric is the Euclidean distance in the two-dimensional vector space, and the dimension reduction module 101 reduces dimension of the composition information vectors 301 of all the plurality of pieces of historical recipe information 105 by using a t-distributed stochastic neighbor embedding (t-SNE) algorithm as the dimension reduction algorithm, to obtain dimension-reduced composition information vectors 302 in the two-dimensional vector space, another measurement method (such as a Manhattan distance or a Chebyshev distance) may be selected for the first distance metric, provided that distances can be assigned for points in the two-dimensional vector space. The dimension reduction module 101 may alternatively reduce dimension of the composition information vectors 301 of all the plurality of pieces of historical recipe information 105 to 3 dimensions by using the t-SNE algorithm, or reduce dimension of the composition information vectors 301 of all the plurality of pieces of historical recipe information 105 to other dimension by using another dimension reduction algorithm. The present invention is not limited to the foregoing embodiments.

Figure 2:
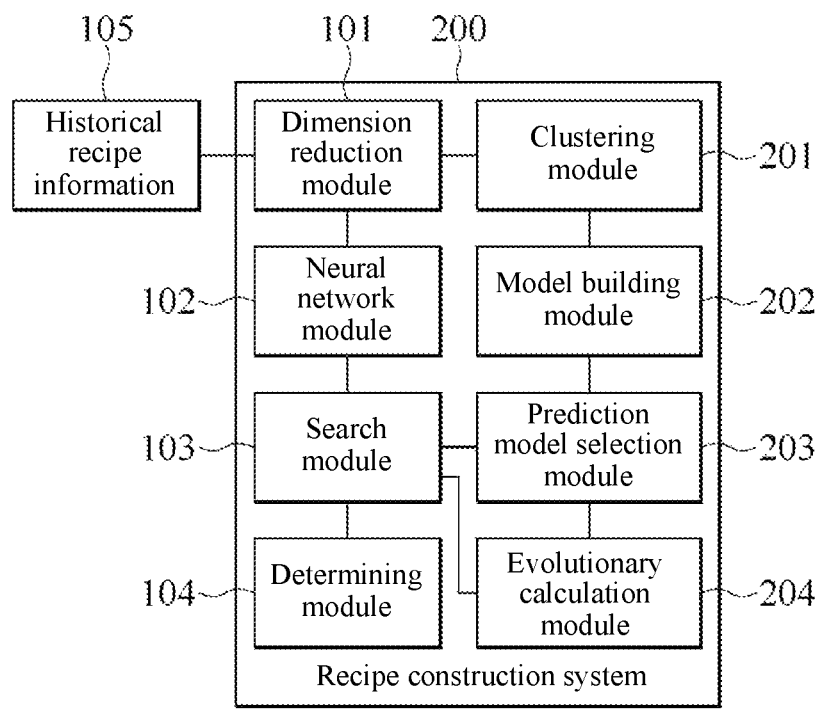
FIG. 2 is a block diagram of a recipe construction system and historical recipe information according to an embodiment of the present invention.
Figure 5:
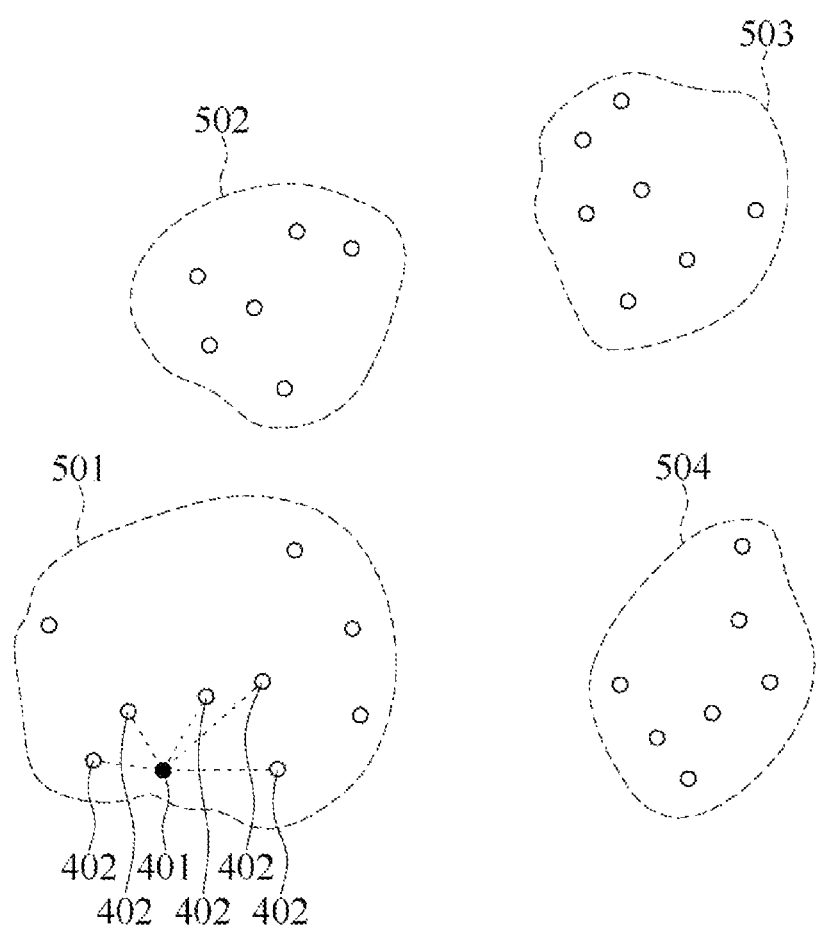
FIG. 5 is a schematic diagram of operation of a clustering module according to an embodiment of the present invention.
Figure 10:
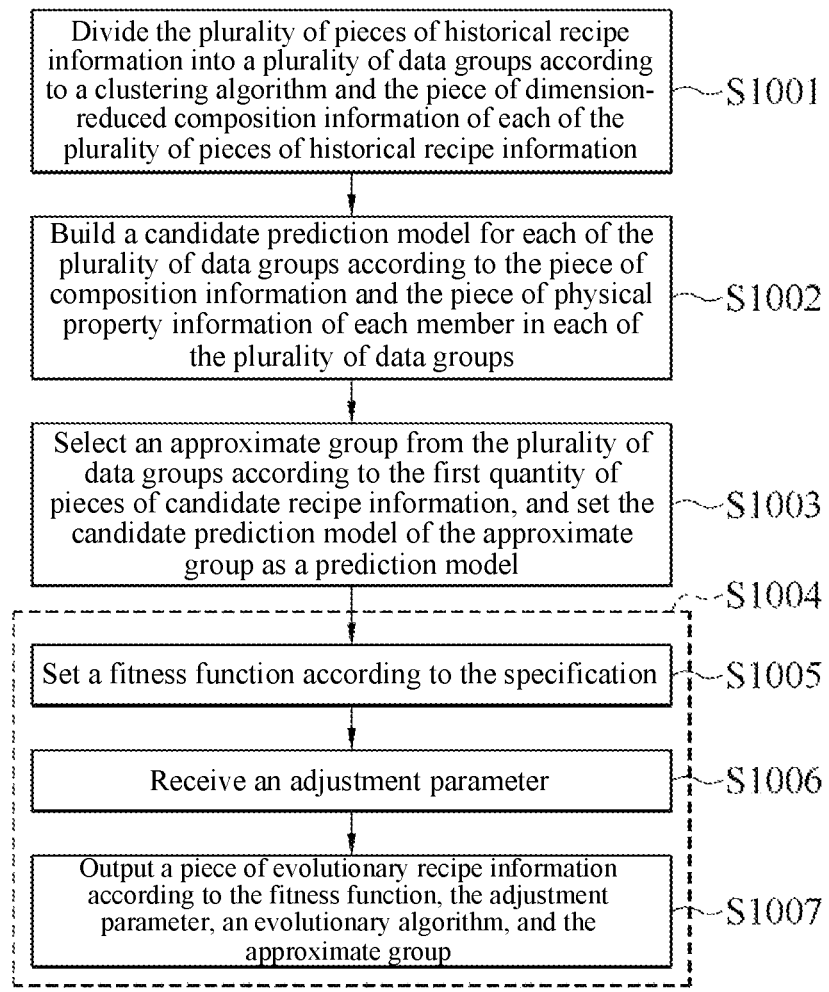
FIG. 10 is a flowchart of a recipe construction method according to an embodiment of the present invention.

FIG. 2 is a block diagram of a recipe construction system 200 and historical recipe information 105 according to an embodiment of the present invention. Referring to FIG. 2, compared with the recipe construction system in FIG. 1A, the recipe construction system 200 shown in FIG. 2 further includes a clustering module 201, a model building module 202, a prediction model selection module 203, and an evolutionary calculation module 204. FIG. 5 is a schematic diagram of operation of a clustering module 201 according to an embodiment of the present invention. FIG. 10 is a flowchart of a recipe construction method according to an embodiment of the present invention. Refer to FIG. 2, FIG. 5, and FIG. 10 together.

In response to that there is no piece of physical property information that meets the specification in the physical property information of the foregoing first quantity of pieces of candidate recipe information, in step S1001, the clustering module 201 divides the plurality of pieces of historical recipe information 105 into a plurality of data groups according to a clustering algorithm and the piece of dimension-reduced composition information of the plurality of each pieces of historical recipe information 105.

In this embodiment, the clustering module 201 uses hierarchical clustering as the clustering algorithm, and divides the plurality of pieces of dimension-reduced composition information into a plurality of data groups according to the content of the piece of dimension-reduced composition information of each of the plurality of pieces of historical recipe information 105. This is illustrated by the example drawn in FIG. 5. As shown in FIG. 5, the clustering module 201 divides the plurality of pieces of dimension-reduced composition information into a plurality of data groups 501, 502, 503, and 504. Correspondingly, the plurality of pieces of historical recipe information 105 are also divided corresponding to the data groups 501, 502, 503, and 504 respectively.

In step S1002, the model building module 202 builds a candidate prediction model for each data group according to the piece of composition information and the piece of physical property information of each member in each data group.

In the example shown in FIG. 5, the model building module 202 builds candidate prediction models for the data groups 501, 502, 503, and 504 according to the piece of composition information and the piece of physical property information of each member in the data groups 501, 502, 503, and 504. In this embodiment, the model building module 202 builds linear models for the data groups 501, 502, 503, and 504 based on the composition information vectors and the physical property information vectors in each of the data groups 501, 502, 503, and 504 by using multivariable linear regression. The linear models are used as candidate prediction models for the data groups.

It should be noted that, in this embodiment, the clustering module 201 uses hierarchical clustering as the clustering algorithm, and the model building module 202 builds candidate prediction models for the data groups 501, 502, 503, and 504 by using multivariable linear regression. In some embodiments of the present invention, the clustering module 201 uses k-means clustering as the clustering algorithm, and the model building module 202 builds candidate prediction models for all of the data groups 501, 502, 503, and 504 by using a fully-connected neural network. The present invention is not limited to the foregoing embodiments as long as the cluster module 201 achieves the purpose of cluster splitting the model building module 202 builds the candidate prediction models for all of the data groups 501, 502, 503, and 504.

In some embodiments of the present invention, the clustering module 201 uses density-based spatial clustering of applications with noise (DBSCAN for short) as the clustering algorithm. In some embodiments of the present invention, the clustering module 201 uses an expectation-maximization algorithm as the clustering algorithm.

In step S1003, the prediction model selection module 203 selects an approximate group from the data groups according to the first quantity of pieces of candidate recipe information, and sets the candidate prediction model of the selected approximate group as a prediction model.

In this embodiment, the prediction model selection module 203 selects the data group with the largest number of the dimension-reduced composition information vectors of the pieces of candidate recipe information as the approximate group. The prediction model selection module 203 further sets the candidate prediction model of the selected approximate group as the prediction model.

In the example shown in FIG. 5, after the prediction model selection module 203 performs counting, the prediction model selection module 203 finds that all the dimension-reduced composition information vectors of the pieces of candidate recipe information (the dimension-reduced composition information vectors 402 in the example shown in FIG. 5) are in the data group 501. Therefore, the prediction model selection module 203 selects the data group 501 as the approximate group. In addition, the prediction model selection module 203 sets the candidate prediction model of the data group 501 as the prediction model.

In step S1004, the evolutionary calculation module 204 performs step S1005 to step S1007. In step S1005, the evolutionary calculation module 204 sets a fitness function according to a specification. In this embodiment, the evolutionary calculation module 204 selects closed intervals that meet physical property limit ranges according to all the physical property limit ranges included in the specification, calculates midpoints of the closed intervals, and then uses a Manhattan distance from the physical property information vector to a vector formed by the midpoints of the closed intervals as the fitness function.

The foregoing specification: tensile strength >13, percentage of elongation >300, viscosity of plastic mixture >20, and compression deformation <10 is used as an example. The evolutionary calculation module 204 selects the closed intervals that meet the physical property limit ranges: tensile strength: [13,15], percentage of elongation: [300, 310], viscosity of plastic mixture: [20,30], and compression deformation: [9,10]. The vector formed by the midpoints of the closed intervals is (14, 305, 25, 9.5). A next objective of the evolutionary calculation module 204 is to calculate a composition information vector, to make the Manhattan distance from a physical property information vector predicted by the prediction model based on the composition information vector to the vector (14, 305, 25, 9.5) formed by the midpoints of the closed intervals as small as possible. Therefore, the evolutionary calculation module 204 selects the Manhattan distance from the physical property vector to a vector (14, 305, 25, 9.5) formed by the midpoints of the closed intervals as the fitness function.

That is, the fitness function may be represented as:

$$f = \sum_{i=1}^{N} |x_i - m_i|$$

where N represents dimension of the physical property information vector, $m_i$ represents a midpoint of each closed interval that meets the physical property limit range, and $x_i$ represents the $i^{th}$ component of the foregoing physical property information vector predicted based on the calculated composition information vector. In this example, $m_1=14$, $m_2=305$, $m_3=25$, and $m_4=9.5$.

The piece of composition information of each of the plurality of pieces of historical recipe information 105 records used ingredients. However, the used ingredients may not be available at a current time. Alternatively, due to cost considerations, use of the ingredients is not considered. Therefore, before calculating a new composition information vector, in step S1006, the evolutionary calculation module 204 first receives an adjustment parameter from the outside. The adjustment parameter indicates which ingredients in the piece of composition information of the plurality of pieces of historical recipe information 105 and to-be-calculated composition information vector are considered and adjustable in the evolutionary calculation, and which ingredients are not considered in the evolutionary calculation. That is, the adjustment parameter indicates a plurality of pieces of adjustable information in the piece of composition information.

Using the foregoing composition information vector (1.0, 2.0, 1.5, 4, 2.3, 1.7, 10) as an example, the first component represents an amount of the first type of principal plastic material, the second component represents an amount of the second type of principal plastic material, and the third component represents an amount of the first type of filler. If use of the first type of principal plastic material is not considered in the evolutionary calculation, the adjustment parameter indicates that use of the first type of principal plastic material is not considered. In the following step S1007, the component of vector corresponding to the first type of principal plastic material is set to 0, so that the component of vector does not participate in the evolutionary calculation. This part is described in detail in the following description.

In this embodiment, the adjustment parameter is implemented by using a list Mask, where MASK is a name of the list. Values in the list Mask include 0 and 1. If a value at the $i^{th}$ position of the list is 0, it indicates that an ingredient represented by a component of a composition information vector corresponding to the position is not considered in the evolutionary calculation. For example, the list Mask=[0, 1, 1, 1, 1, 1, 1]. The first list element of the list Mask is 0 in this example, it indicates that an ingredient (the first type of principal plastic material in this example) corresponding to the first component in the composition information vector is not considered in the evolutionary calculation. However, the second list element to the seventh list element of the list Mask are 1, it indicates that ingredients corresponding to the second component to the seventh component in the composition information vector are considered in the evolutionary calculation.

In step S1007, the evolutionary calculation module 204 outputs a piece of evolutionary recipe information according to the fitness function, the adjustment parameter, an evolutionary algorithm, and the approximate group.

Figure 11:
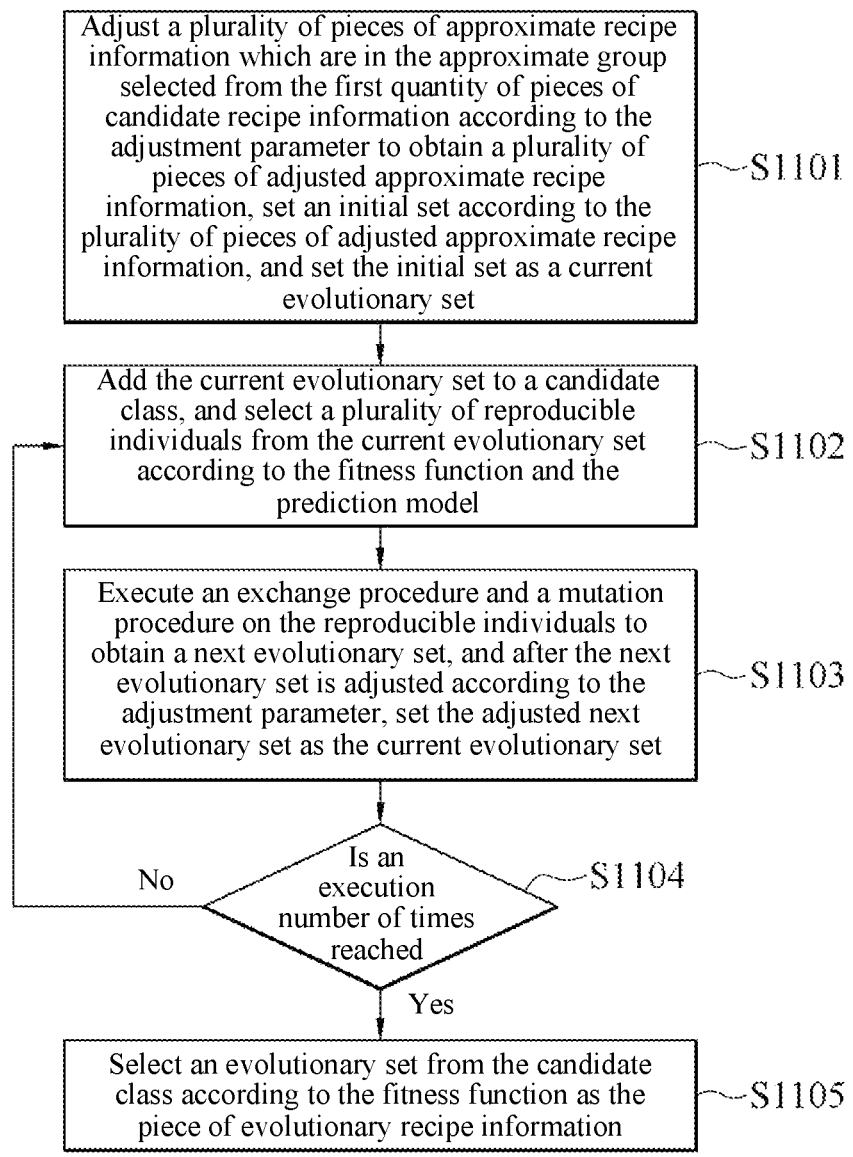
FIG. 11 is a flowchart of an evolutionary calculation according to an embodiment of the present invention.

There are various types of evolutionary algorithms. FIG. 11 is a flowchart of an evolutionary calculation according to an embodiment of the present invention. The foregoing step S1007 includes step S1101 to step S1105 shown in FIG. 11. Referring to FIG. 2, FIG. 5, and FIG. 11 together. In step S1003, the prediction model selection module 203 selects the data group with the largest number of the dimension-reduced composition information vectors of the pieces of candidate recipe information as the approximate group, in step S1101, the evolutionary calculation module 204 then selects the pieces of candidate recipe information in the approximate group as a plurality of pieces of approximate recipe information, and adjusts, according to an adjustment parameter, the piece of composition information of each of the plurality of pieces of approximate recipe information to obtain a plurality of pieces of adjusted approximate recipe information. The evolutionary calculation module 204 sets an initial set according to the plurality of pieces of adjusted approximate recipe information, and then sets the initial set as a current evolutionary set.

The example shown in FIG. 5 is used for description herein. In step S1003, the prediction model selection module 203 selects the data group 501 with the largest number of the dimension-reduced composition information vectors of the pieces of candidate recipe information as the approximate group. The evolutionary calculation module 204 then selects the pieces of candidate recipe information in the approximate group. In this example, the pieces of candidate recipe information are the pieces of historical recipe information corresponding to five dimension-reduced composition information vectors 402. If the historical recipe information vectors of the historical recipe information corresponding to the five dimension-reduced composition information vectors 402 are respectively:

first: a composition information vector (1, 2, 3, 4, 5, 6, 7, 8), and a physical property information vector (23, 62, 34.99);
second: a composition information vector (1.1, 2, 3, 4.1, 5, 6, 7.1, 8), and a physical property information vector (0, 20, 41.14);
third: a composition information vector (1.1, 2, 3, 4.1, 5, 6, 7.1, 8), and a physical property information vector (1, 25, 42.89);
fourth: a composition information vector (1.2, 2.2, 3, 4.3, 5, 6, 7.1, 8), and a physical property information vector (2, 19, 48.80); and
fifth: a composition information vector (1.4, 2, 3.3, 4.1, 5, 6, 7.1, 8.1), and a physical property information vector (3, 20, 41.81), and the adjustment parameter is a list Mask=[1, 1, 1, 0, 0, 0, 1, 1], then five adjusted approximate recipe information vectors obtained according to the adjustment parameter are respectively:

first: an adjusted composition information vector (1, 2, 3, 0, 0, 0, 7, 8), and a physical property information vector (23, 62, 34.99);
second: an adjusted composition information vector (1.1, 2, 3, 0, 0, 0, 7.1, 8), and a physical property information vector (0, 20, 41.14);
third: an adjusted composition information vector (1.1, 2, 3, 0.0, 0, 7.1, 8), and a physical property information vector (1, 25, 42.89);
fourth: an adjusted composition information vector (1.2, 2.2, 3, 0, 0, 0, 7.1, 8), and a physical property information vector (2, 19, 48.80); and
fifth: an adjusted composition information vector (1.4, 2, 3.3, 0, 0, 0, 7.1, 8.1), and a physical property information vector (3, 20, 41.81).

The evolutionary calculation module 204 then adds the adjusted composition information vectors in the five adjusted approximate recipe information vectors to the initial set, and then expands the initial set to have a fixed quantity of offspring. There are many methods of expansion, in some embodiments, the evolutionary calculation module 204 directly copies the existing adjusted composition information vectors in the initial set to expand the initial set to a fixed quantity of offspring. In some embodiments, the evolutionary calculation module 204 randomly selects one composition information vector from the initial set, then adds a random real number within a range to a value of an ingredient indicated by the list Mask as needing to be considered in the evolutionary calculation as a new composition information vector, calculates a physical property information vector of the new composition information vector by using the prediction model, and adds the new composition information vector and the physical property information vector thereof to the initial set until the initial set is expanded to have a quantity of offspring.

In step S1102, the evolutionary calculation module 204 adds the current evolutionary set to a candidate class, to record the current evolutionary set calculated each time. In addition, the evolutionary calculation module 204 selects a plurality of reproducible individuals from the current evolutionary set according to the fitness function and the prediction model.

In this embodiment, the evolutionary calculation module 204 calculates fitness function values of all members in the current evolutionary set, and then sorts all the members in the current evolutionary set in ascending order according to the fitness function values of all the members. A minimum value in the fitness function values of all the members is defined as a representative fitness function value of the current evolutionary set in the present invention. The evolutionary calculation module 204 then selects an evolutionary quantity of members in the current evolutionary set as reproducible individuals according to this sorting.

In step S1103, an exchange procedure and a mutation procedure are sequentially performed on the reproducible individuals whose quantity is the evolutionary quantity, to obtain a next evolutionary set, and as described in the foregoing step S1003, the next evolutionary set is set as the current evolutionary set after being adjusted according to the adjustment parameter.

In step S1104, step S1102 and step S1103 are repeatedly performed until a quantity of repetitions reaches a preset quantity of executions.

Finally, in step S1105, the determining module 104 selects one evolutionary set from the candidate class according to the fitness function, where the representative fitness function value of the evolutionary set is a minimum representative fitness function value of all the evolutionary sets in the candidate class. The determining module 104 outputs the selected evolutionary set as a piece of evolutionary recipe information.

Figure 6A:
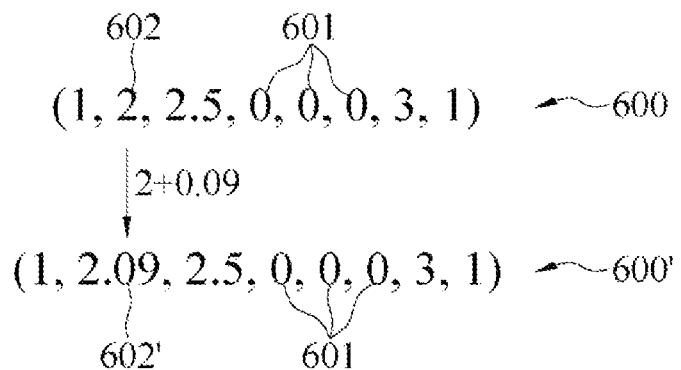
FIG. 6A is a schematic diagram of operation of a mutation procedure according to an embodiment of the present invention.
Figure 6B:
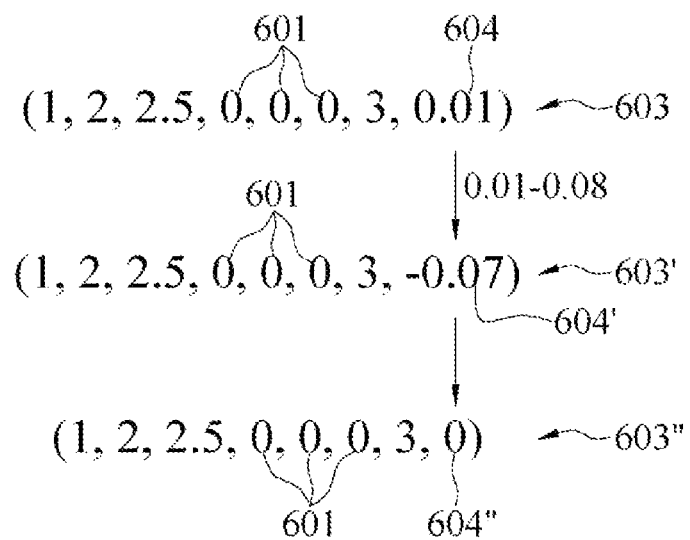
FIG. 6B is a schematic diagram of operation of a mutation procedure according to an embodiment of the present invention.
Figure 7:
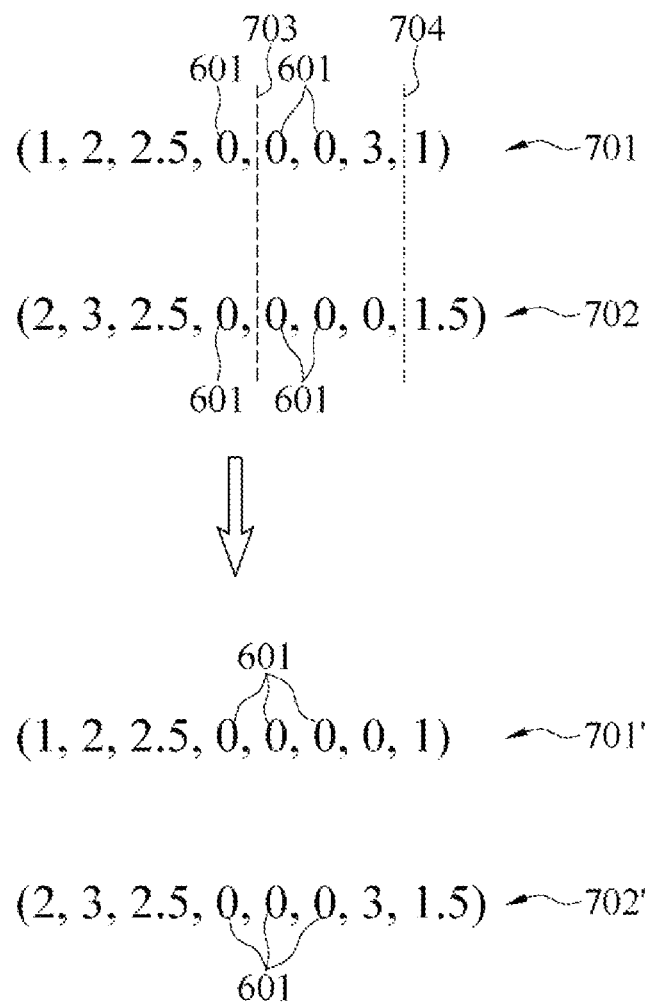
FIG. 7 is a schematic diagram of operation of an exchange procedure according to an embodiment of the present invention.
Figure 12:
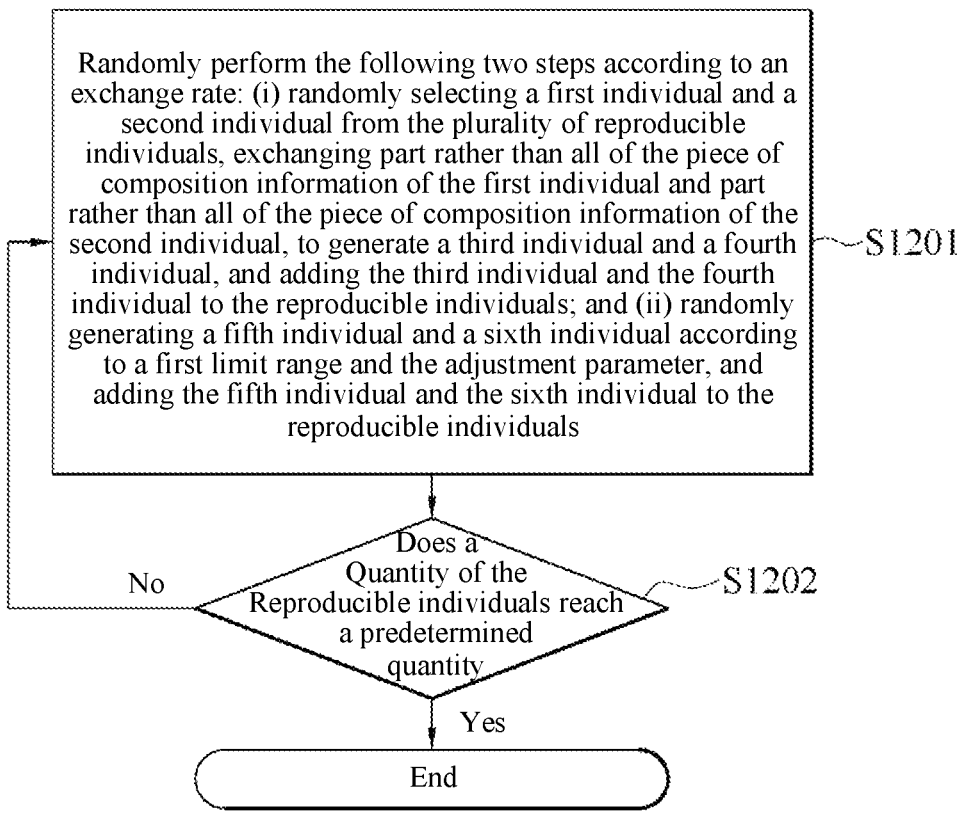
FIG. 12 is a flowchart of an exchange procedure according to an embodiment of the present invention.
Figure 13:
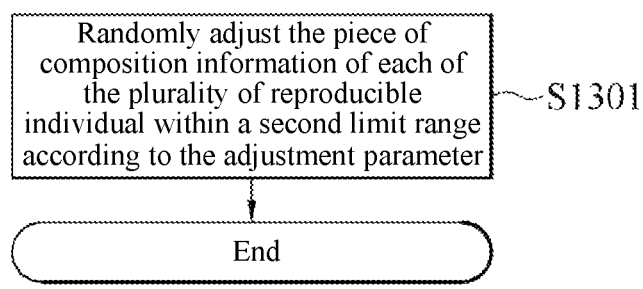
FIG. 13 is a flowchart of a mutation procedure according to an embodiment of the present invention.

FIG. 6A and FIG. 6B are schematic diagrams of operation of a mutation procedure according to an embodiment of the present invention. FIG. 7 is a schematic diagram of operation of an exchange procedure according to an embodiment of the present invention. FIG. 12 is a flowchart of an exchange procedure according to an embodiment of the present invention. FIG. 13 is a flowchart of a mutation procedure according to an embodiment of the present invention. Refer to FIG. 6A, FIG. 6B, FIG. 7, FIG. 12, and FIG. 13 together.

In step S1102, the evolutionary calculation module 204 selects a plurality of reproducible individuals from the current evolutionary set according to a fitness function and a prediction model. In step S1201, the evolutionary calculation module 204 randomly performs the following two steps according to an exchange rate: (i) Randomly select a first individual and a second individual from the plurality of reproducible individuals, and exchange part rather than all of the piece of composition information of the first individual and part rather than all of the piece of composition information of the second individual, to generate a third individual and a fourth individual. The evolutionary calculation module 204 adds the third individual and the fourth individual to the reproducible individuals. (ii) Randomly generate a fifth individual and a sixth individual according to a first limit range and an adjustment parameter, and add the fifth individual and the sixth individual to the reproducible individuals.

In this embodiment, the exchange rate is a real number in the range of [0, 1], which represents a probability of performing the foregoing step (i). The evolutionary calculation module 204 could use a random function in common software that simulates randomness, for example, the random( ) function of the random module in Python. The random( ) function randomly generates a real number in a range of [0, 1). The evolutionary calculation module 204 uses the random( ) function of the random module in Python and the following program structure:

if random.random( )<exchange rate:
  perform the foregoing step (i)
else:
  perform the foregoing step (ii), to make the step recorded in the foregoing (i) perform with the probability of the exchange rate, and the step recorded in the foregoing (ii) perform with the probability of (1−exchange rate). For example, if the exchange rate is 0.7, the program structure described above performs step (i) with a probability of 0.7, and performs step (ii) with a probability of 0.3.

In step (i), the evolutionary calculation module 204 randomly selects a first individual and a second individual from the reproducible individuals (by using the sample( ) function of the random module in Python), then randomly selects two cut-off points (two integers in the range of the length of the composition information vector selected by using the randint ( ) function of the random module in Python), and exchanges content of the component between the two cut-off points in the composition information vector of the first individual and content of a the component between the two cut-off points in the composition information vector of the second individual. The example shown in FIG. 7 is used for description. The component 601 of the composition information vector is a part indicated by the adjustment parameter as not being considered, and therefore is adjusted to 0. The evolutionary calculation module 204 randomly selects the first individual and the second individual from the reproducible individuals. The composition information vector of the first individual is 701, and the composition information vector of the second individual is 702. The evolutionary calculation module 204 randomly selects two cut-off points 703 and 704, and then exchanges content of components between the two cut-off points 703 and 704, to generate a composition information vector 701' and a composition information vector 702'. The evolutionary calculation module 204 calculates a physical property information vector of the composition information vector 701' by using the prediction model to generate a third individual. The evolutionary calculation module 204 calculates a physical property information vector of the composition information vector 702' by using the prediction model to generate a fourth individual. The evolutionary calculation module 204 adds the third individual and the fourth individual to the reproducible individuals.

In step (ii), the evolutionary calculation module 204 randomly generates, according to a first limit range [−2, 2] and an adjustment parameter, a real number in a range of [−2, 2] for a component of a composition information vector indicated by the adjustment parameter as needing to be considered, to generate two composition information vectors. The evolutionary calculation module 204 calculates physical property information vectors corresponding to the two composition information vectors by using the prediction model to generate a fifth individual and a sixth individual, and adds the fifth individual and the sixth individual to the reproducible individuals. For example, Mask=[0, 1, 1, 1, 1, 1, 1]. The two randomly generated composition information vectors are (0, 0.1, −0.3, 1, 1.5, 1, 1) and (0, 1, 1, 1.5, 0.2, −1.7, 0.8). Then, corresponding physical property information vectors, for example, (2, 33, 7) and (3, 44, 5), are calculated by using the prediction model. In this case, it is set as follows:

fifth individual: a composition information vector (0, 0.1, −0.3, 1, 1.5, 1, 1), and a physical property information vector (2, 33, 7); and sixth individual: a composition information vector (0, 1, 1, 1.5, 0.2, −1.7, 0.8), and a physical property information vector (3, 44, 5).

In step S1202, the evolutionary calculation module 204 determines whether a quantity of reproducible individuals reaches a predetermined quantity. In this embodiment, the predetermined quantity is the fixed quantity of offspring mentioned above.

It should be noted that, the predetermined quantity does not need to be the quantity of offspring, and may alternatively be greater than the quantity of offspring. After generating the predetermined quantity of reproducible individuals, the evolutionary calculation module 204 performs other processing. The present invention is not limited thereto.

After performing the exchange procedure, the evolutionary calculation module 204 performs the mutation procedure. In step S1301, the piece of composition information of each of the plurality of reproducible individual is adjusted within a second limit range according to an adjustment parameter.

In this embodiment, the evolutionary calculation module 204 adds, for the piece of composition information of each reproducible individual according to second limit ranges (0.01, 0.1) and (−1, −0.01) (by using the uniform( ) function of the random module in Python), real numbers randomly generated in (0.01, 0.1) and (−1, −0.01) to a component of a composition information vector indicated by the adjustment parameter as needing to be considered, to generate a mutated composition information vector. The evolutionary calculation module 204 calculates a physical property information vector corresponding to the mutated composition information vector by using the prediction model to generate a mutated reproducible individual.

In an embodiment, after adding the real numbers randomly generated in (0.01, 0.1) and (−1, −0.01), the evolutionary calculation module 204 further checks whether the value of the component of the mutated composition information vector is proper. If after restoring the value of the component of the mutated composition information to a dose in actual manufacturing, the evolutionary calculation module 204 finds that when the restored dose in actual manufacturing is a negative value, it indicates that the value of the component of the mutated composition information vector is improper. Therefore, the value of the component of the mutated composition information vector is set to 0.

The example shown in FIG. 6A is used for description. In this example, Mask=[1,1,1,0,0,0,1,1]. The component 601 of the composition information vector 600 is a part indicated by the adjustment parameter as not being considered. The evolutionary calculation module 204 randomly generates a real number 0.09 plus a value 602 of the second component of the composition information vector 600 (an actual value is 2) according to the second limit ranges (0.01, 0.1) and (−1, −0.01) to obtain a new value 602' of the second component (an actual value is 2.09), thereby generating a new composition information vector 600'.

The example shown in FIG. 6B is used for description. In this example, Mask=[1,1,1,0,0,0,1,1]. The component 601 of the composition information vector 603 is a part indicated by the adjustment parameter as not being considered. The evolutionary calculation module 204 randomly generates a real number −0.08 plus a value 604 of the eighth component of the composition information vector 603 (an actual value is 0.01) according to the second limit ranges (0.01, 0.1) and (−1, −0.01) to obtain a new value 604' of the eighth component (an actual value is −0.07), thereby generating a new composition information vector 603'. However, the evolutionary calculation module 204 determines that the value of −0.07 is improper (in this example, it is assumed that a mean of the eighth components is 0). Therefore, the value of the eighth component is set to 0 to obtain a new value 604" of the eighth component, thereby generating a new composition information vector 603".

It should be noted that, the initial composition information vector in the foregoing embodiments may be evaluated by experts in advance. In this case, the recipe construction systems 100, 100' and 200 disclosed in the embodiments of the present invention may fully integrate knowledge included in the initial composition information vector and the plurality of pieces of historical recipe information 105. Certainly, the initial composition information vector in the foregoing embodiments may alternatively be randomly generated. The recipe construction systems 100, 100', and 200 disclosed in the embodiments of the present invention may use knowledge included in the plurality of pieces of historical recipe information 105 to find a piece of composition information that meets the specification. In an embodiment of the present invention, the recipe construction system 200 uses a composition information vector in the outputted piece of evolutionary recipe information as the initial composition information vector.

Additionally, it should be noted that, although in the foregoing description, a random selection function is implemented by using a built-in function in the random module in Python, and a random execution step is implemented by using the built-in function in the random module in Python in cooperation with the if structure in the Python syntax. Certainly, the random selection function may alternatively be implemented by using a built-in function of the <random> library in the C++ language standard library, and the random execution step is implemented by using the built-in function of the <random> library in the C++ language with the if structure in a C++ syntax. Alternatively, the random selection function may be implemented by using a function of generating a random number included in another programming language, and the random execution step is performed by using a function of generating a random number included in another programming language in cooperation with a structure of a conditional branch instruction in a programming language syntax. The present invention is not limited thereto.

Figure 8:
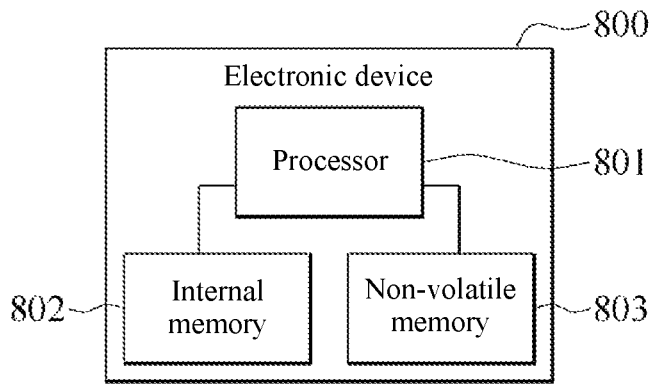
FIG. 8 is a schematic structural diagram of an electronic device according to an embodiment of this specification.

FIG. 8 is a schematic structural diagram of an electronic device 800 according to an embodiment of this specification. As shown in FIG. 8, at a hardware level, the electronic device 800 includes a processor 801, an internal memory 802, and a non-volatile memory 803. The internal memory 802 is, for example, a random access memory (RAM). The non-volatile memory is, for example, at least one magnetic disk memory. Certainly, the electronic device 800 may further include hardware required for other functions.

The internal memory 802 and the non-volatile memory 803 are configured to store programs. The programs may include program code, and the program code includes computer operation instructions. The internal memory 802 and the non-volatile memory 803 provide instructions and data to the processor 801. The processor 801 reads a corresponding computer program from the non-volatile memory 803 to the internal memory 802 and then runs the computer program, to form a recipe construction system 100, 100', or 200 at a logical level. The processor 801 is further configured to perform the steps recorded in FIG. 9 to FIG. 13.

The processor 801 may be an integrated circuit chip having a signal processing capability. During implementation, the methods and the steps disclosed in the foregoing embodiments may be completed through hardware integrated logic circuits in the processor 801 or instructions in the form of software. The processor 801 may be a general purpose processor, including a central processing unit (CPU), a digital signal processor (DSP), an application-specific integrated circuit (ASIC), a field-programmable gate array (FPGA), or another programmable logic device, and may implement or perform the methods and the steps disclosed in the foregoing embodiments.

An embodiment of this specification further provides a computer readable storage media. The computer readable storage media store at least one instruction, and the at least one instruction, when executed by a processor 801 of the electronic device 800, may cause the processor 801 of the electronic device 800 to perform the methods and the steps disclosed in the foregoing embodiments.

Examples of a storage medium of a computer include, but are not limited to, a phase-change memory (PRAM), a static random access memory (SRAM), a dynamic random access memory (DRAM), another type of RAM, a read-only memory (ROM), an electrically erasable programmable read-only memory (EEPROM), a flash memory or another internal memory technology, a compact disc read-only memory (CD-ROM), a digital versatile disc (DVD) or another optical storage device, a cassette tape, a magnetic tape storage or another magnetic storage device, or any other non-transmission medium, which may be configured to store information accessible by a computing device. Based on the definition in this specification, the computer readable media includes no transitory media such as a modulated data signal and a carrier.

What is claimed is:

1. A computer-implemented recipe construction system, including:
    a dimension reduction module, configured to receive a plurality of pieces of historical recipe information, and obtain a piece of dimension-reduced composition information of each of the plurality of pieces of historical recipe information according to a piece of composition information of each of the plurality of pieces of historical recipe information and a dimension reduction algorithm;
    a neural network module, configured to receive a piece of initial composition information, wherein the neural network module is configured to train a plurality of neural network parameters of the neural network module according to the piece of composition information and the piece of dimension-reduced composition information of each of the plurality of pieces of historical recipe information to obtain a plurality of trained neural network parameters, and obtain a piece of dimension-reduced initial composition information according to the trained neural network parameters and the piece of initial composition information;
    a search module, configured to search the plurality of pieces of historical recipe information for a first quantity of pieces of candidate recipe information according to a first distance metric, the piece of dimension-reduced initial composition information, and the piece of dimension-reduced composition information of each of the plurality of pieces of historical recipe information;
    a determining module, configured to determine whether a piece of physical property information of each the first quantity of pieces of candidate recipe information meets a specification, and output a piece of solution recipe information in response to the piece of physical property information of the piece of solution recipe information in the first quantity of pieces of candidate recipe information meets the specification; and
    a standardization module, configured to receive a plurality of pieces of original historical recipe information and a piece of original initial composition information, wherein each of the plurality of pieces of original historical recipe information comprises the piece of physical property information and a piece of original composition information, the standardization module obtains a plurality of standardization parameters according to the piece of original composition information of each of the plurality of pieces of original historical recipe information, the standardization module obtains the plurality of pieces of historical recipe information and the piece of composition information of each of the plurality of pieces of historical recipe information according to the plurality of standardization parameters and the plurality of pieces of original historical recipe information, and the standardization module obtains the piece of initial composition information according to the standardization parameters and the piece of original initial composition information.

2. The computer-implemented recipe construction system according to claim 1, further comprising:
    a clustering module, configured to divide the plurality of pieces of historical recipe information into a plurality of data groups according to a clustering algorithm and the piece of dimension-reduced composition information of each of the plurality of pieces of historical recipe information;
    a model building module, configured to build a candidate prediction model for each of the plurality of data groups according to the piece of composition information and the piece of physical property information of a member in each of the plurality of data groups;
    a prediction model selection module, configured to select an approximate group from the plurality of data groups according to the first quantity of pieces of candidate recipe information, and set the candidate prediction model of the approximate group as a prediction model; and
    an evolutionary calculation module, configured to perform the following steps:
    (a) setting a fitness function according to the specification;
    (b) receiving an adjustment parameter; and
    (c) outputting a piece of evolutionary recipe information according to the fitness function, the adjustment parameter, an evolutionary algorithm, and the approximate group, wherein the adjustment parameter indicates a plurality of pieces of adjustable information in the piece of composition information of each member in the approximate group.

3. The computer-implemented recipe construction system according to claim 2, wherein step (c) comprises the following steps:
  (c1) selecting a plurality of pieces of approximate recipe information which are in the approximate group from the first quantity of pieces of candidate recipe information, adjusting the piece of composition information of each of the plurality of pieces of approximate recipe information according to the adjustment parameter to obtain a plurality of pieces of adjusted approximate recipe information, setting an initial set according to the plurality of pieces of adjusted approximate recipe information, and setting the initial set as a current evolutionary set;
  (c2) adding the current evolutionary set to a candidate class, and selecting a plurality of reproducible individuals from the current evolutionary set according to the fitness function and the prediction model;
  (c3) sequentially executing an exchange procedure and a mutation procedure on the reproducible individuals to obtain a next evolutionary set, and after the next evolutionary set is adjusted according to the adjustment parameter, setting the adjusted next evolutionary set as the current evolutionary set; and
  (c4) repeating step (c2) and step (c3) an execution number of times, wherein
  the determining module is configured to select an evolutionary set from the candidate class according to the fitness function as the piece of evolutionary recipe information.

4. The computer-implemented recipe construction system according to claim 3, wherein the exchange procedure comprises the following steps:
  (c31) randomly performing the following two steps according to an exchange rate:
  (i) randomly selecting a first individual and a second individual from the plurality of reproducible individuals, exchanging part rather than all of the piece of composition information of the first individual and part rather than all of the piece of composition information of the second individual, to generate a third individual and a fourth individual, and adding the third individual and the fourth individual to the plurality of reproducible individuals; and (ii) randomly generating a fifth individual and a sixth individual according to a first limit range and the adjustment parameter, and adding the fifth individual and the sixth individual to the reproducible individuals; and
  (c32) repeating step (c31) until a quantity of the reproducible individuals reaches a predetermined quantity.

5. The computer-implemented recipe construction system according to claim 3, wherein the mutation procedure comprises the following step:
  randomly adjusting the piece of composition information of each of the plurality of reproducible individuals within a second limit range according to the adjustment parameter.

6. The computer-implemented recipe construction system according to claim 1, wherein the dimension reduction algorithm is a non-linear algorithm.

7. The computer-implemented recipe construction system according to claim 6, wherein the dimension reduction algorithm is a t-distributed stochastic neighbor embedding (t-SNE) algorithm.

8. A recipe construction method, performed by a processor, the recipe construction method comprising:
  receiving a plurality of pieces of historical recipe information, and obtaining a piece of dimension-reduced composition information of each of the plurality of pieces of historical recipe information according to a piece of composition information of each of the plurality of pieces of historical recipe information and a dimension reduction algorithm;
  receiving a piece of initial composition information, training a plurality of neural network parameters of a neural network module according to the piece of composition information and the piece of dimension-reduced composition information of each of the plurality of pieces of historical recipe information to obtain a plurality of trained neural network parameters, and obtaining a piece of dimension-reduced initial composition information according to the trained neural network parameters and the piece of initial composition information;
  searching the plurality of pieces of historical recipe information for a first quantity of pieces of candidate recipe information according to a first distance metric, the piece of dimension-reduced initial composition information, and the piece of dimension-reduced composition information of each of the plurality of pieces of historical recipe information; and
  determining whether a piece of physical property information of each the first quantity of pieces of candidate recipe information meets a specification, and outputting a piece of solution recipe information in response to the piece of physical property information of the piece of solution recipe information in the first quantity of pieces of candidate recipe information meets the specification; the recipe construction method further comprising:
  receiving a plurality of pieces of original historical recipe information and a piece of original initial composition information, wherein each of the plurality of pieces of original historical recipe information comprises the piece of physical property information and a piece of original composition information;
  obtaining a plurality of standardization parameters according to the piece of original composition information of each of the plurality of pieces of original historical recipe information;
  obtaining the plurality of pieces of historical recipe information and the piece of composition information of each of the plurality of pieces of historical recipe information according to the plurality of standardization parameters and the plurality of pieces of original historical recipe information, and
  obtaining the piece of initial composition information according to the standardization parameters and the piece of original initial composition information.

9. The recipe construction method according to claim 8, further comprising:
  dividing the plurality of pieces of historical recipe information into a plurality of data groups according to a clustering algorithm and the piece of dimension-reduced composition information of each of the plurality of pieces of historical recipe information;
  building a candidate prediction model for each of the plurality of data groups according to the piece of composition information and the piece of physical property information of each member in each of the plurality of data groups;

selecting an approximate group from the plurality of data groups according to the first quantity of pieces of candidate recipe information, and setting the candidate prediction model of the approximate group as a prediction model; and performing the following steps of an evolutionary calculation:

(a) setting a fitness function according to the specification;
(b) receiving an adjustment parameter; and
(c) outputting a piece of evolutionary recipe information according to the fitness function, the adjustment parameter, an evolutionary algorithm, and the approximate group, wherein the adjustment parameter indicates a plurality of pieces of adjustable information in the piece of composition information of each member in the approximate group.

10. The recipe construction method according to claim 9, wherein the step (c) of the evolutionary calculation comprises steps:

(c1) adjusting a plurality of pieces of approximate recipe information which are in the approximate group selected from the first quantity of pieces of candidate recipe information according to the adjustment parameter to obtain a plurality of pieces of adjusted approximate recipe information, setting an initial set according to the plurality of pieces of adjusted approximate recipe information, and setting the initial set as a current evolutionary set;

(c2) adding the current evolutionary set to a candidate class, and selecting a plurality of reproducible individuals from the current evolutionary set according to the fitness function and the prediction model;

(c3) executing an exchange procedure and a mutation procedure on the reproducible individuals to obtain a next evolutionary set, and after the next evolutionary set is adjusted according to the adjustment parameter, setting the adjusted next evolutionary set as the current evolutionary set;

(c4) repeating step (c2) and step (c3) an execution number of times; and (c5) selecting an evolutionary set from the candidate class according to the fitness function as the piece of evolutionary recipe information.

11. The recipe construction method according to claim 10, wherein the exchange procedure comprises:

(c31) randomly performing the following two steps according to an exchange rate:
(i) randomly selecting a first individual and a second individual from the plurality of reproducible individuals, exchanging part rather than all of the piece of composition information of the first individual and part rather than all of the piece of composition information of the second individual, to generate a third individual and a fourth individual, and adding the third individual and the fourth individual to the reproducible individuals; and
(ii) randomly generating a fifth individual and a sixth individual according to a first limit range and the adjustment parameter, and adding the fifth individual and the sixth individual to the reproducible individuals; and (c32) repeating step (c31) until a quantity of the reproducible individuals reaches a predetermined quantity.

12. The recipe construction method according to claim 10, wherein the mutation procedure comprises:

randomly adjusting the piece of composition information of each of the plurality of reproducible individual within a second limit range according to the adjustment parameter.

13. The recipe construction method according to claim 8, wherein the dimension reduction algorithm is a non-linear algorithm.

14. The recipe construction method according to claim 13, wherein the dimension reduction algorithm is a t-distributed stochastic neighbor embedding (t-SNE) algorithm.

15. A computer readable recording media with stored programs, wherein after loading and executing the stored programs, a processor performs the method according to claim 8.

16. A non-transitory computer program product, storing at least one instruction, wherein the at least one instruction, when executed by a processor, causes the processor to perform the method according to claim 8.

* * * * *